United States Patent
Brown et al.

(10) Patent No.: US 10,039,519 B2
(45) Date of Patent: Aug. 7, 2018

(54) RADIOTHERAPY BEAM ALIGNMENT WITH FIDUCIAL PHANTOM IMAGING

(71) Applicant: Elekta AB (publ), Stockholm (SE)

(72) Inventors: Kevin John Brown, West Sussex (GB); David Anthony Roberts, West Sussex (GB); Janusz Harasimowicz, Surrey (GB); Martin Sell, West Sussex (GB); Julian Byrne, West Sussex (GB); Armin Fuerst, Geitendorf (GB)

(73) Assignee: Elekta AB (publ), Stockholm (SE)

( * ) Notice: Subject to any disclaimer, the term of this patent is extended or adjusted under 35 U.S.C. 154(b) by 330 days.

(21) Appl. No.: 14/524,987

(22) Filed: Oct. 27, 2014

(65) Prior Publication Data
US 2016/0114190 A1 Apr. 28, 2016

(30) Foreign Application Priority Data
Oct. 28, 2013 (GB) .................................. 1318974.1

(51) Int. Cl.
*A61B 6/00* (2006.01)
*A61N 5/10* (2006.01)

(52) U.S. Cl.
CPC .............. *A61B 6/584* (2013.01); *A61B 6/583* (2013.01); *A61N 5/1048* (2013.01);
(Continued)

(58) Field of Classification Search
CPC .... A61B 6/00; A61B 6/40; A61B 6/54; A61B 6/58; A61B 6/582–6/584; A61B 2560/00;
(Continued)

(56) References Cited

U.S. PATENT DOCUMENTS

| 2002/0085668 A1* | 7/2002 | Blumhofer | A61B 6/547 378/68 |
| 2006/0002519 A1* | 1/2006 | Jenkins | A61N 5/1048 378/207 |
| 2011/0305380 A1* | 12/2011 | Bose | A61N 5/1075 382/132 |

FOREIGN PATENT DOCUMENTS

EP 2394701 A1 12/2011

OTHER PUBLICATIONS

Mao, W. et al. "Initial application of a geometric QA tool for integrate MV and kV imaging systems on three image guided radiotherapy systems", Medical Physics 38(5), May 2011 (pp. 2335-2341).

(Continued)

*Primary Examiner* — Anastasia Midkiff
(74) *Attorney, Agent, or Firm* — Finnegan, Henderson, Farabow, Garrett & Dunner LLP

(57) ABSTRACT

A method of aligning the radiation beam in a radiotherapy system comprising a source for producing a beam of radiation and an imaging device for imaging from the beam, both mounted to be rotatable about an axis, a fiducial phantom between the source and imaging device, the method comprising: rotating the beam and imaging device in a trajectory about the axis while obtaining images of the fiducial phantom from a plurality of different angles, at least one image including a feature of the imaging apparatus, adjusting the trajectory of the source relative to that feature to position the isocenter substantially in the center of the volume, determining from each image of the fiducial phantom the position of the source at the rotational position the image was obtained, and calculating the center of rotation of the positions of the source to define the isocenter of the system.

20 Claims, 4 Drawing Sheets

(52) U.S. Cl.
CPC .............. *A61N 5/1075* (2013.01); *A61B 6/582* (2013.01); *A61B 2560/0228* (2013.01); *A61N 5/1049* (2013.01); *A61N 2005/1052* (2013.01); *A61N 2005/1055* (2013.01); *A61N 2005/1076* (2013.01)

(58) Field of Classification Search
CPC ........ A61B 2560/02; A61B 2560/0223; A61B 2560/0228; A61B 2560/0233; A61B 2560/0238; A61N 5/10; A61N 5/103; A61N 5/1031; A61N 5/1039; A61N 5/1048; A61N 5/1049; A61N 5/1075; A61N 2005/1052; A61N 2005/1055; A61N 2005/1061; A61N 2005/1076
See application file for complete search history.

(56) References Cited

OTHER PUBLICATIONS

M. Mamalui-Hunger, "Linac mechanic AQ using a Cylindrical Phantom", Physics in Medicine and Biology 53, Aug. 22, 2008 (UK), (pp. 5139-5149).

GB Search Report of PCT/GB2013/18974 (Application No. GB1318974.1), dated May 20, 2014.

J. Chetley Ford, Dandan Zheng and Jeffrey F Williamson. "Estimation of CT cone-beam geometry using a novel method insensitive to phantom fabrication inaccuracy: Implications for isocenter localization accuracy." American Association of Medical Physics, *Med. Phys.* 38 (6), Jun. 2011, 2829-2840.

Weihua Mao, Louis lee and Lei Xing. "Development of a QA phantom and automated analysis tool for geometric quality assurance of on-board MV and kV X-ray imaging systems". *Med. Phys.* 35 (4), Apr. 2008, 1497-1506.

Youngbin Cho, Douglas J. Moseley, Jeffrey H Siewerdsen and David A Jaffray. "Accurate technique for complete geometric calibration of cone-beam computed tomography systems". *Med. Phys.* 32 (4), Apr. 2005, 968-983.

\* cited by examiner

RADIOTHERAPY BEAM ALIGNMENT WITH FIDUCIAL PHANTOM IMAGING

CROSS-REFERENCE TO RELATED PATENT APPLICATION

This U.S. patent application claims priority under 35 U.S.C, § 119 to United Kingdom Patent Application No, 1318974.1, filed Oct. 28, 2013, which is incorporated herein by reference in its entirety.

FIELD OF THE INVENTION

The present invention relates to techniques for radiotherapeutic beam alignment in radiation therapy apparatus, particularly but not exclusively in linear accelerator apparatus and Magnetic Resonance (MR)-guided linear accelerator apparatus.

BACKGROUND ART

A radiotherapeutic apparatus is well known, and consists of a source of radiation which emits a beam of radiation that is directed toward a patient in order to destroy or otherwise harm cancerous cells within the patient. Usually, the beam is collimated in order to limit its spatial extent to a desired region within the patient, usually the tumour or a sub-section of the tumour, and to avoid irradiating nearby healthy and/or sensitive tissue. The source can be a linear accelerator for high-energy (MV) X-radiation, or an isotopic source such as Co-60. The source is often mounted on a rotatable gantry, so as to be rotated around the patient in order to irradiate the desired region from a number of different directions, thereby reducing the dose applied to healthy tissue around the desired region. The collimator can move to change the shape of the beam as the source rotates, in order to build up a complex dose distribution for tumours with more challenging shapes and/or which are located near to sensitive areas. An electronic portal imaging device (EPID) may be mounted to the gantry on the opposite side to the source so as to receive the beam once it has been attenuated by passage through the patient; this device produces an image which can be used for correctly aligning or calibrating the system, as well as for assessing the patient's location and the placement of the radiotherapeutic treatment.

Incorporating real-time image guidance into radiotherapy can improve tumour targeting accuracy, enabling better avoidance of critical structures and reducing side effects. Such guidance is of particular benefit if a non-ionizing imaging technique such as MRI (magnetic resonance imaging) is employed. Work is currently being undertaken to integrate a linear accelerator with an MR scanner; integrating high-quality MRI with a linear accelerator (creating an "MR Linac", or MRL) allows tissue to be tracked online, and therapeutic radiation beams can be guided to their targets (which may be moving and deforming, such as when the patient breathes) with sub-millimeter precision during treatment.

Such is the precision with which treatment is to be applied to a patient, it is necessary to align the radiotherapeutic beam with the magnetic field of the MR scanner with a very high degree of accuracy before the patient can be positioned accurately with respect to the apparatus and the radiotherapeutic treatment begun; this degree of accuracy necessitates taking into account mechanical effects, such as sagging or deflection of elements of the apparatus due to gravity (which can vary according to the rotational position of the gantry) such as the source and the EPID or other imaging device, variations in the alignment of the source so that the beam is not directed perpendicularly to the EPID, and other factors which cause the beam, or its trajectory as the gantry rotates, to deviate from the intended path. In linear accelerators used for radiotherapy, cone-beam computed tomography (CBCT) techniques which employ phantoms have been utilised to address the issue of beam alignment (see, for example, J. Chetley Ford, Dandan Zheng and Jeffrey F Williamson. "Estimation of CT cone-beam geometry using a novel method insensitive to phantom fabrication inaccuracy: Implications for isocenter localization accuracy." American Association of Medical Physics, Med. Phys. 38 (6), June 2011, 2829-2840.; Weihua Mao, Louis lee and Lei Xing. "Development of a QA phantom and automated analysis tool for geometric quality assurance of on-board MV and kV X-ray imaging systems". Med. Phys. 35 (4), April 2008, 1497-1506; and Youngbin Cho, Douglas J. Moseley, Jeffrey H Siewerdsen and David A Jaffray. "Accurate technique for complete geometric calibration of cone-beam computed tomography systems". Med. Phys. 32 (4), April 2005, 968-983), but conventional techniques are not readily transferable to MRLs, firstly because there is restricted space in the bore of the MR scanner (so restricted that it is not feasible to use lasers or other light projection systems to assist in aligning the beam correctly), and secondly because phantoms visible to X-ray imagers are not usually visible to an MR scanner. Moreover, conventional approaches are incapable of accurately aligning both the beam and the beam imaging device, accounting for all the factors affecting their deviation from the ideal, nor can they be used for the alignment of associated equipment, such as a beam collimator, nor to align the beam so that its profile (on the beam imaging device, or EPID, and hence on the patient) is symmetrical (referred to hereinafter as "beam symmetry").

SUMMARY OF THE INVENTION

The present invention therefore provides, in a first aspect, in a radiotherapy system comprising a source for producing a beam of radiation and a device for imaging from the beam, both mounted so as to be rotatable about an axis, and an imaging apparatus having a volume within which imaging takes place, a method of aligning the beam using a fiducial phantom between the source and the device, the method comprising: rotating the beam and device in a trajectory about the axis while obtaining a plurality of images of the fiducial phantom from a plurality of different angles, wherein at least one image includes a feature of the imaging apparatus, adjusting the trajectory of the source relative to that feature so as to position the isocenter substantially centrally of the volume, determining from each image of the fiducial phantom the position of the source at the rotational position the image was obtained, and calculating the center of rotation of the positions of the source to define the isocenter of the system.

The term "fiducial phantom" used herein means a device used for determining beam geometries which incorporates a plurality of markers (usually at least 4) which are visible to the particular imaging device and the associated radiation used to illuminate the device. These markers could be similar to those described in our co-pending British patent application, No. GB1305751.8, and the phantom could be symmetric or non-symmetric, similar to those described in our co-pending British patent application, No. GB1318958.4. The term "isocenter" means, for any rotational position of the source, the point on the plane in which the beam is rotated by the gantry which intersects with the instantaneous axis of rotation of the source (i.e. the axis of rotation of the source at that rotational position). The imaging apparatus may be an MRI apparatus in an MRL, or it may be a Positron Emission Tomography (PET) apparatus.

Such an arrangement is able to account accurately for the movement of the instantaneous geometric center of rotation of the beam as the beam rotates (caused by the deviation factors described above) and, because it requires only a radiotherapeutic beam, an associated imager (e.g. an EPID), both of which form part of most MRLs, and a phantom, it can easily be used in an MRL, and without requiring any laser system or the like. It effectively produces a "map" showing the deviation of the positions of the source and the imaging device from their ideal positions as the gantry carrying them rotates. In addition, it enables the beam to be aligned with accuracy with respect to the imaging device and with ancillary equipment such as a beam collimator, and to increase beam symmetry, as will be explained.

The method may further comprise calibrating the trajectory in relation to the gantry angle through analysis of at least one non-symmetric feature of the fiducial phantom as seen in each image, and/or its position/movement between images, relative to the isocenter. Our co-pending British patent application, No. GB1318958.4 describes such a fiducial phantom. In this way, the isocenter position during rotation can be accurately matched to the true physical position of the gantry (this can be likened to the accurate aligning of a clock face: the steps described three paragraphs above this one establish, for each point around the circumference of rotation, the isocenter position (similar to the numbers on the clock face), while the method of this paragraph allows the positions of the points on the circumference to be properly located (i.e. so that the number "12" on the clock face is vertically uppermost). This allows the EPID alignment to be defined using the coordinate system obtained by calculating the average location of the isocenter of the beam and the deviation of the isocenter from this average position.

Where the radiotherapy apparatus in question comprises an MRI apparatus in which there is a predetermined imaging volume, the method comprises detecting in at least one image a feature of the MRI apparatus, and adjusting the trajectory of the source relative to that feature so as to position the isocenter substantially in the center of the volume. This allows the source of radiotherapeutic radiation to be positioned so as to be aligned approximately with, and the beam directed approximately at, the center of the volume. Often this volume is located between the two cryogenically-cooled, superconducting coil sections of the MR scanner, so it is relatively easy to position the source approximately (guided by the design of the mechanical parts involved, for example, or even simply by eye); then, the image of a feature, such as the edge(s) of these coils, or some other object whose position relative to the center of the imaging volume is known to a good degree of accuracy, can be used to determine by what amount the isocenter is offset from the center of the volume, and the appropriate adjustment made to move the isocenter towards the center of the volume. Iteration of this process at a plurality of rotational positions enables the isocenter to be located at or very close to the center of the volume for all rotational positions of the gantry.

Provided that the fiducial phantom comprises markers visible to MRI, the method may further comprise scanning the fiducial phantom with an MR scanner. This allows the source to be accurately aligned with the magnetic field of the MR scanner.

Where the system comprises a collimator adjacent the source and having collimating edges (which are usually but not always parallel) to collimate the beam, the method may comprise positioning the collimator edges so that when illuminated by the beam they cast shadows which are projected onto and visible to the device, determining from an image of the fiducial phantom the position of the source and the position of the shadows of the edges relative to the isocenter, and adjusting the position of the source and/or the collimator along an axis substantially transverse to the edges so as to position the shadows of the edges centrally about the isocenter. This applies whether the imaging apparatus is an MRI or a PET apparatus.

It is known that the when the electron beam from a linear accelerator impinges on the target it produces a radiation beam that has an intensity distribution that has a maximum in a direction that is substantially aligned with the incident electron beam. It is a desired characteristic that this maximum intensity is centrally positioned with respect to the isocenter, thereby creating a symmetric intensity distribution about this point. The image of the beam obtained from the device may be analysed to determine the magnitude of its asymmetry of intensity, and adjustments made to the beam so as to reduce the asymmetry. This may comprise rotating the beam about an axis perpendicular to the axis of the beam so as to locate the highest intensity part of the beam towards the center of the image. The rotation of the beam may be effected by rotating the source (independently of the gantry) and/or by adjusting the direction of the beam emitted from the source (such as by "tilting" the waveguide within a linear accelerator, by adjusting the angle of the electron beam within the accelerator by the use of magnetic or electric forces).

The rotating may be about an axis substantially parallel to the collimator edges and, where the collimator is a multi-leaf collimator (MLC), parallel to the axis of movement of the leaves of the MLC. This serves to align the beam in a first plane (which can suitably be the X-Z plane where the Z axis is substantially vertical) so that it impinges substantially squarely onto the imaging device. Additionally or alternatively the rotating may be about an axis perpendicular to the collimator edges, this serving to align the beam with the MLC and in the Y-Z plane.

There may be a requirement to locate an object between the source and the device, such as another imaging device; provided that the object comprises at least one marker adapted to be visible in an image produced by the beam in the device, the method may further comprise obtaining an image of the object and, from the position and/or orientation of the marker(s), determining the position and/or orientation of the object.

There may be a requirement to position a second imaging device between the source and the first imaging device, such as to provide a larger image than is available from the first device (such as where the edges of the superconducting coil of an MR scanner limit the width of the beam which can be detected by the first imaging device). In this case the method may further comprise irradiating an object with the beam and obtaining images thereof simultaneously in both the said device for imaging and the second imaging device in pairs of images, and comparing the position of at least one feature of the object in at least one pair of simultaneous images to determine the position of the second imaging device relative to the isocenter. In this case, features of the object common to image pairs from both imaging devices can be used to calculate accurately the position of the second imaging device relative to the system, so that the positions of features unique to the second imaging device (which may be in the bore of the MR scanner, for example) can be accurately extrapolated.

Methods in accordance with the first aspect of the invention may be used in MRLs and also in radiotherapy apparatus where there is no MR scanner but instead a PET scanner. They may be used for initial calibration and commissioning of apparatus, for setting apparatus up pre-treatment and for quality assurance purposes.

In a second aspect, the invention also provides, in a radiotherapy system comprising a source for producing a beam of radiation and a device for imaging from the beam, both mounted so as to be rotatable about an axis, and a collimator having collimating edges to collimate the beam, a method of aligning the beam using a fiducial phantom between the source and the device, the method comprising: positioning the collimator edges so that when illuminated by the beam they cast shadows which are projected onto and visible to the device; determining from an image of the fiducial phantom the position of the source and the position of the shadows of the edges relative to the isocenter, and adjusting the position of the source and/or the collimator along an axis substantially transverse to the edges so as to position the shadows of the edges centrally about the isocenter; rotating the beam and device in a trajectory about the axis while obtaining a plurality of images of the fiducial phantom from a plurality of different angles; determining from each image of the fiducial phantom the position of the source at the rotational position the image was obtained, and calculating the center of rotation of the positions of the source to define the isocenter of the system. Such an arrangement allows the radiotherapeutic beam to be rapidly and accurately aligned using features of the collimator in the images.

Additionally or alternatively the trajectory may be calibrated in relation to the gantry angle through analysis of at least one non-symmetric feature of the fiducial phantom as seen in each image. Where the fiducial phantom comprises markers visible to MRI, the method may further comprise scanning the fiducial phantom with an MR scanner which has an imaging field so as to align the source with the imaging field. The image of the beam obtained from the device may be analysed to determine the magnitude of its asymmetry of intensity; this may comprise rotating the beam about an axis perpendicular to the axis of the beam so as to reduce the asymmetry of intensity, and the rotation may be about an axis substantially parallel to the collimator edges, and/or about an axis substantially perpendicular to the collimator edges.

As with the first aspect of the invention, where there is a requirement to locate an object between the source and the device, such as another imaging device, then provided that the object comprises at least one marker adapted to be visible in an image produced by the beam in the device, the method may further comprise obtaining an image of the object and, from the position and/or orientation of the marker(s), determining the position and/or orientation of the object. And, where a second imaging device is positioned between the source and the said device for imaging, the method may further comprise irradiating an object with the beam and obtaining images thereof simultaneously in both the said device for imaging and the second imaging device in pairs of images, and comparing the position of at least one feature of the object in at least one pair of simultaneous images to determine the position of the second imaging device relative to the isocenter.

Methods in accordance with the second aspect of the invention may be used in any form of radiotherapy apparatus where there is a scanner. They may be used for initial calibration and commissioning of apparatus, for setting apparatus up pre-treatment and for quality assurance purposes.

BRIEF DESCRIPTION OF THE DRAWINGS

The invention will now be described by way of example and with reference to the accompanying figures in which.

DETAILED DESCRIPTION OF THE EMBODIMENTS

Figure 1:
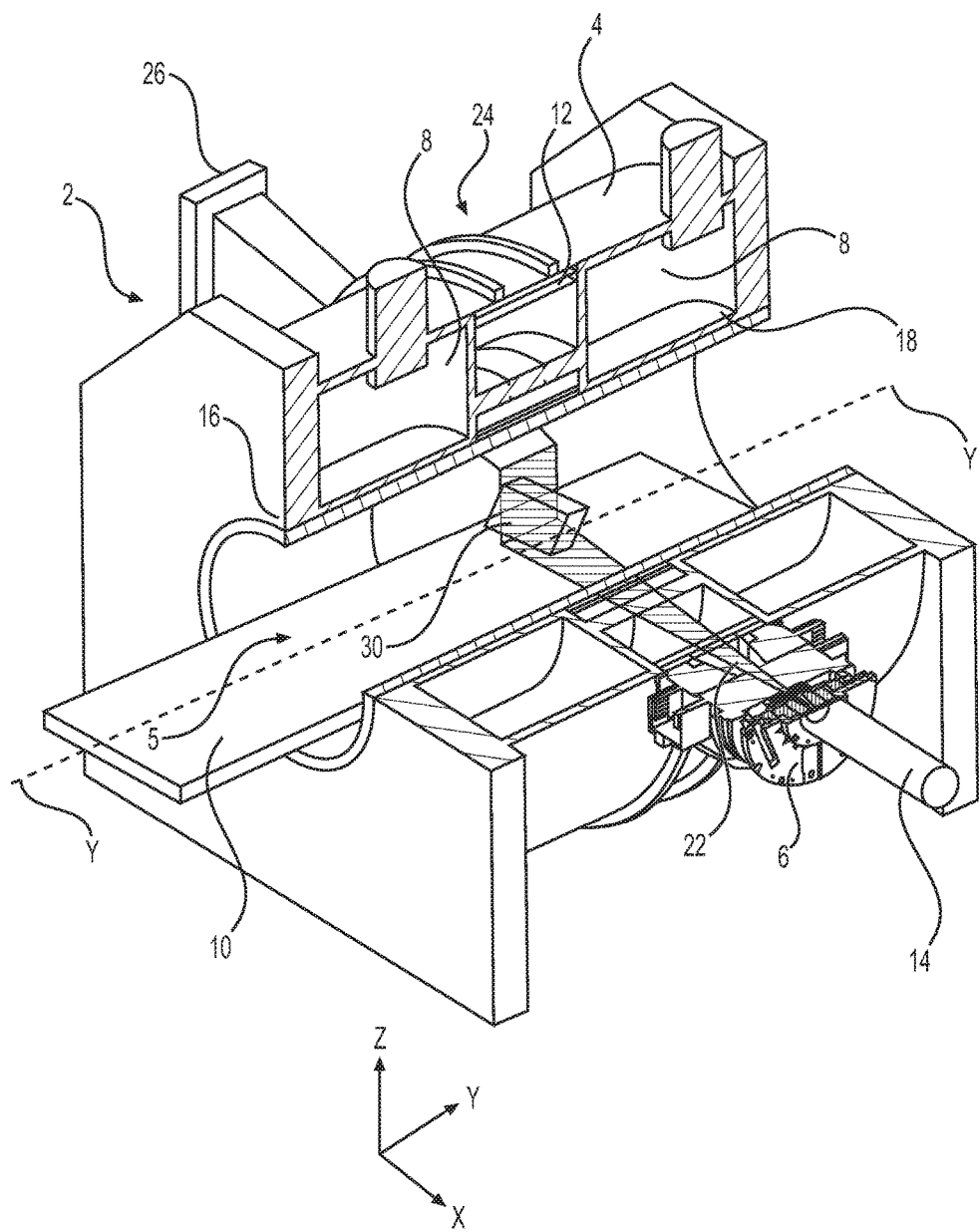
FIG. 1 is a schematic view, in partial cross-section, of an MRI-guided radiotherapy (MRL) system.

FIG. 1 shows a system 2 comprising a radiotherapy apparatus 6 and a magnetic resonance imaging (MRI) apparatus 4. The system includes a couch 10, for supporting a patient in the apparatus. The couch 10 is movable along a horizontal, translation axis (labelled "Y"), such that a patient resting on the couch is moved into the bore 5 of the MRI apparatus 4 and into the path of the radiotherapy apparatus 6. In one embodiment, the couch 10 is rotatable around a central vertical axis of rotation, transverse to the translation axis, although this is not illustrated. The couch 10 may form a cantilever section that projects away from a support structure (not illustrated). In one embodiment, the couch 10 is moved along the translation axis relative to the support structure in order to form the cantilever section, i.e. the cantilever section increases in length as the couch is moved and the lift remains stationary. In another embodiment, both the support structure and the couch 10 move along the translation axis, such that the cantilever section remains substantially constant in length, as described in our U.S. patent application Ser. No. 11/827,320 filed on 11 Jul. 2007.

As mentioned above, the system 2 also comprises an MRI apparatus 4, for producing near real-time imaging of a patient positioned on the couch 10. The MRI apparatus includes a primary magnet 8 which acts to generate the so-called "primary" magnetic field for magnetic resonance imaging. That is, the magnetic field lines generated by operation of the magnet 8 run substantially parallel to the central translation axis I. The primary magnet 8 consists of one or more coils with an axis that runs parallel to the translation axis Y; though not shown, the coils may be coaxial with the translation axis. The one or more coils may be a single coil or a plurality of coaxial coils of different diameter. As illustrated, the one or more coils in the primary magnet 8 are spaced such that a central window 12 of the magnet 8 is free of coils. In other embodiments, the coils in the magnet 8 may simply be thin enough that they are substantially transparent to radiation of the wavelength generated by the radiotherapy apparatus. The magnet 8 may further comprise one or more active shielding coils, which generates a magnetic field outside the magnet 8 of approximately equal magnitude and opposite polarity to the external primary magnetic field. The more sensitive parts of the system 2, such as the accelerator 14, are positioned in this region outside the magnet 8 where the magnetic field is cancelled, at least to a first order.

The MRI apparatus 4 further comprises two gradient coils 16, 18, which generate the so-called "gradient" magnetic field that is superposed on the primary magnetic field. These coils 16, 18 generate a gradient in the resultant magnetic field that allows spatial encoding of the protons so that their position can be determined, for example the gradient coils 16, 18 can be controlled such that the imaging data obtained has a particular orientation. The gradient coils 16, 18 are positioned around a common central axis with the primary magnet 16, and are displaced from one another along that central axis. This displacement creates a gap, or window, between the two coils 16, 18. In an embodiment where the primary magnet 8 also comprises a central window between coils, the two windows are aligned with one another.

An RF system causes the protons to alter their alignment relative to the magnetic field. When the RF electromagnetic field is turned off the protons return to the original magnetization alignment. These alignment changes create a signal which can be detected by scanning. The RF system may include a single coil that both transmits the radio signals and receives the reflected signals, dedicated transmitting and receiving coils, or multi-element phased array coils, for example. Control circuitry controls the operation of the various coils 8, 16, 18 and the RF system, and signal-processing circuitry receives the output of the RF system, generating therefrom images of the patient supported by the couch 10.

As mentioned above, the system 2 further comprises a radiotherapy apparatus 6 which delivers doses of radiation to a patient supported by the couch 10. The majority of the radiotherapy apparatus 6, including at least a source of radiation 14 (e.g. an x-ray source and a linear accelerator) and a multi-leaf collimator (MLC) 22, is mounted on a chassis 24. The chassis 24 is continuously rotatable around the couch 10 when it is inserted into the treatment area, powered by one or more chassis motors. In the illustrated embodiment, a radiation detecting and imaging device 26 such as an EPID is also mounted on the chassis 24 opposite the radiation source 14 and with the rotational axis of the chassis positioned between them. The radiotherapy apparatus 6 further comprises control circuitry, which (with the RF control circuitry) may be integrated within the system 2 shown in FIG. 1 or remote from it, and controls the radiation source 14, the MLC 22 and the chassis motor.

The radiation source 14 is positioned to emit a beam of radiation through the window defined by the two gradient coils 16, 18, and also through the window 12 defined in the primary magnet 8. The radiation beam may be a cone beam or a fan beam, for example.

In operation, a patient is placed on the couch 10 and the couch is inserted into the treatment area defined by the magnetic coils 16, 18 and the chassis 24. The control circuitry controls the radiation source 14, the MLC 22 and the chassis motor to generate a beam of radiotherapeutic radiation and to deliver radiation to the patient through the window 12 between the coils 16, 18. The chassis motor is controlled such that the chassis 24 rotates about the patient, meaning the radiation can be delivered from different directions. The MLC 22 has a plurality of elongate leaves oriented orthogonal to the beam axis; an example is illustrated and described in our EP-A-0,314,214, to which the reader is directed in order to obtain a full understanding of the described embodiment. The leaves of the MLC 22 are controlled to move (along the Y-axis in FIG. 1) to take different positions blocking or allowing through some or all of the radiation beam, thereby altering the shape of the beam as it will reach the patient. Simultaneously with rotation of the chassis 24 about the patient, the couch 10 may be moved along a translation axis into or out of the treatment area (i.e. parallel to the axis of rotation of the chassis). With this simultaneous motion a helical radiation delivery pattern is achieved.

The MRI apparatus 4, and specifically the signal-processing circuitry, delivers real-time (or in practice near real-time) imaging data of the patient to the control circuitry. This information allows the control circuitry to adapt the operation of the MLC 22, for example, such that the radiation delivered to the patient accurately tracks the motion of the target region, for example due to breathing, so that the radiation received by the patient is in accordance with a predetermined treatment plan contained within a treatment planning system, or TPS (not shown). All the control circuitry and the TPS may be integrated in one or more computer processors, so as collectively to ensure that the patient is treated in accordance with the predetermined plan.

Figure 5:
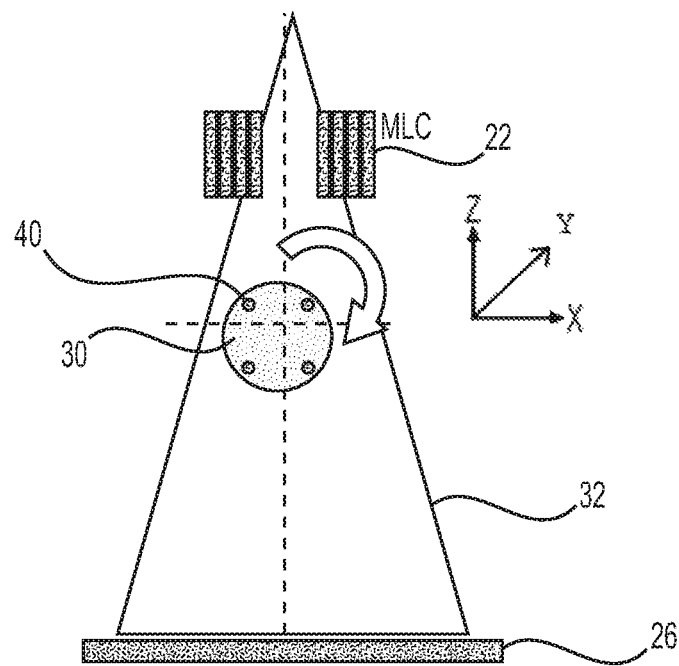

To accurately align the beam from the radiotherapy apparatus 6 a fiducial phantom 30 is placed within the bore 5 of the MR scanner 4 in the path of the beam produced by the apparatus 6 and imaged by the device 26 at a plurality of angles of rotation of the apparatus 6 in the X-Z plane. At least one of the plurality of images includes a feature of the imaging apparatus 4. By comparing the positions in the images of the various markers 40 (as shown in FIG. 5) which form an essential part of the phantom 30, the TPS can determine the position of the source at the rotational position each image was obtained, and calculate the center of rotation 36 of the positions of the source relative to the first feature to define the isocenter 34 of the system. A feature of the imaging apparatus may include the edge of one of the coils 16, 18. The position, in an image of an edge of one of the coils 16, 18, that defines the edge of the window 12, is used to position the isocenter of the beam centrally within the imaging volume in the bore 5. Defining the isocenter can be made without reference to the external geometry of the system 2, such as if the phantom is symmetrical and images are taken at regular angular intervals (if the images are taken every 90 degrees of a symmetrical phantom, it will not be possible to determine whether the isocenter in each image is of the phantom when the gantry is at the first, second, third or fourth rotational position as the images will appear identical). It is therefore necessary to use a phantom which has at least one feature of asymmetry when defining the isocenter without reference to the external geometry of the system; analysing this at least one non-symmetric feature of the fiducial phantom as seen in each image enables the isocenter to be correlated with the gantry angle.

Figure 2:
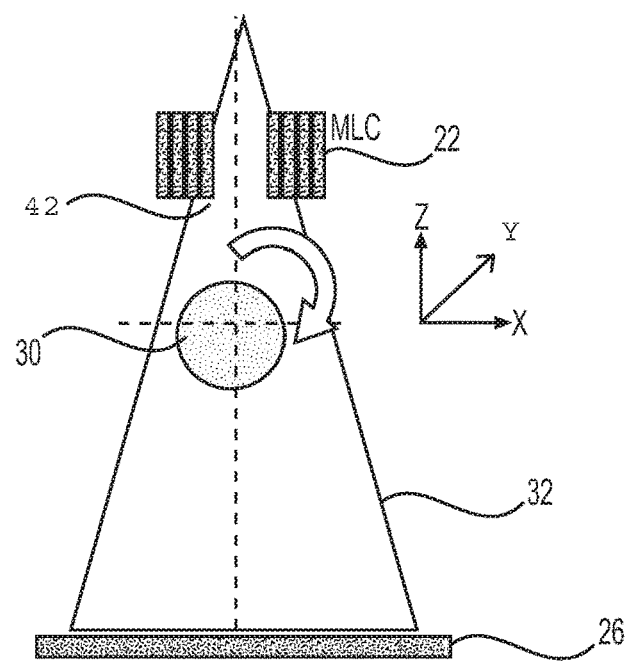
FIG. 2 is a schematic view showing the alignment process for the system of FIG. 1 in the X-Z plane.
Figure 3:
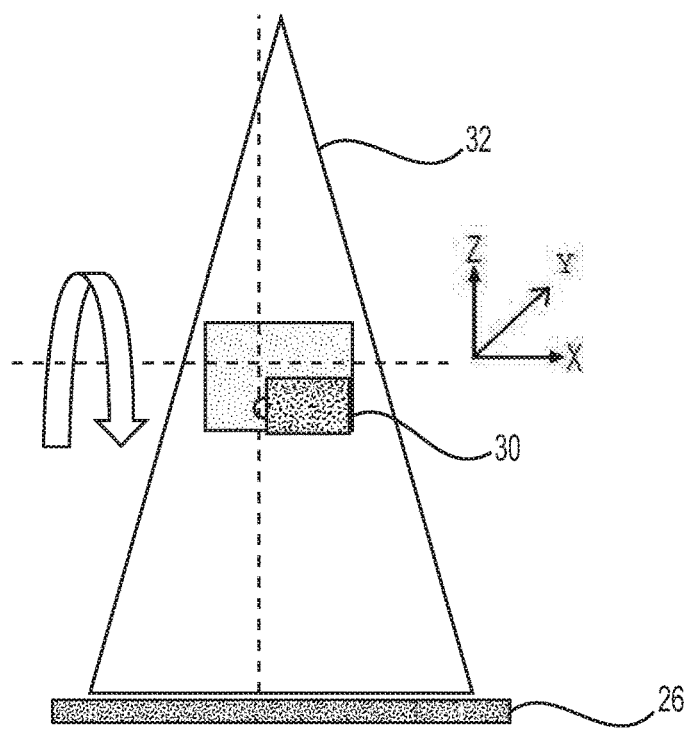
FIG. 3 is a schematic view showing the alignment process in the Y-Z plane for the system of FIG. 1.
Figure 4:
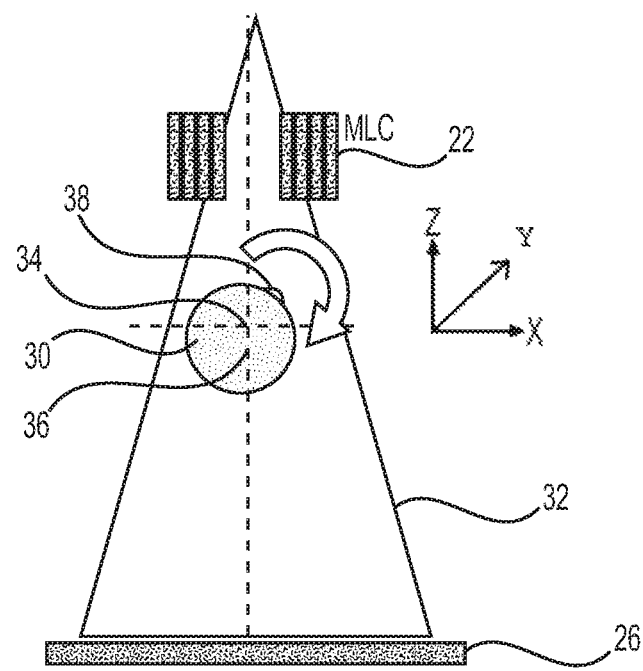
Figure 6:
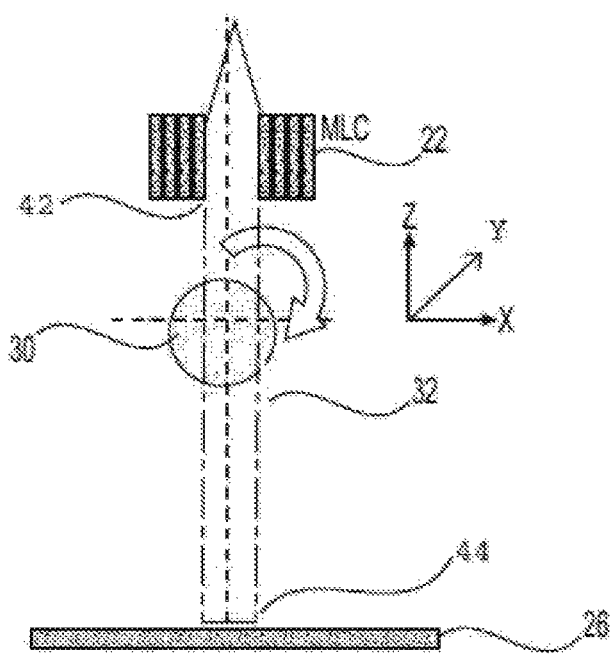

Referring to FIG. 2, the fiduciary phantom 30 is shown within the beam 32 of radiotherapeutic radiation extending towards the imaging device 26, as seen along the Y axis. The MLC 22 is positioned with its leaves movable along the Y axis and, as already described, the images of the phantom obtained can be used to adjust the position of the beam 32 relative to the device 26 in the X direction. The images obtained by the device 26 include one or both of the shadows 44 cast by the edges 42 of the MLC 22 (as further shown in FIG. 6), and thus the isocenter of the beam 32 may be positioned centrally on the detection area of the device 26. Tilting the beam 32 around the Y axis, as indicated by the arrow in the drawing, can alter the intensity of the image, so as to reduce asymmetry of beam intensity in the X-Z plane and therefore ensure that the beam 32 is correctly (usually perpendicularly) directed towards the plane (the X-Y plane as shown) of the device 26. Similarly, as shown in FIG. 3, asymmetry of beam intensity in the Y-Z plane may be reduced by rotating the beam 32 about the X axis, as shown by the arrow in FIG. 3. As shown in FIG. 4, the fiducial phantom 30 may include a non-symmetric feature 38 such that the orientation can be determined more accurately when imaged.

It will of course be understood that many variations may be made to the above-described embodiment without departing from the scope of the present invention. Where different variations or alternative arrangements are described above, it should be understood that embodiments of the invention may incorporate such variations and/or alternatives in any suitable combination.

The invention claimed is:

1. A method performed in a radiotherapy system, the radiotherapy system comprising a source for producing a beam of radiation, a first imaging device for imaging from the beam, the source and the first imaging device mounted so as to be rotatable about an axis perpendicular to the direction of the beam, and a second imaging device having a volume within which imaging takes place, the method aligning the beam using a fiducial phantom including a plurality of markers, the fiducial phantom being located between the source and the first imaging device, the method comprising:
rotating the source and the first imaging device in a trajectory about the axis while obtaining a plurality of images of the fiducial phantom from a plurality of different angles, wherein at least one image of the plurality of images includes a first feature of the second imaging device;
adjusting the trajectory of the source relative to the first feature so as to position the isocenter substantially in the center of the volume;
determining, from the locations of the markers in each image of the fiducial phantom, a position of the source at the rotational position the image was obtained; and
calculating the center of rotation of the positions of the source to define the isocenter of the radiotherapy system.

2. The method according to claim 1, wherein the fiducial phantom includes at least one non-symmetric feature when viewed from the first imaging device, the method further comprising:
calibrating the trajectory in relation to a gantry angle through analysis of the at least one non-symmetric feature of the fiducial phantom included in each image.

3. The method according to claim 1, wherein the second imaging device is a Magnetic Resonance Imaging (MRI) apparatus.

4. The method according to claim 3, wherein the fiducial phantom comprises markers visible to MRI, the method further comprising:
scanning the fiducial phantom with a Magnetic Resonance (MR) scanner which has an imaging field so as to align the source with the imaging field.

5. The method according to claim 4, wherein the system comprises a collimator having collimating edges to collimate the beam, the method comprising:
positioning the collimator edges so that when the collimator edges are illuminated by the beam, the collimator edges cast shadows projected onto and visible to the first imaging device,
determining, from an image of the fiducial phantom, the position of the source and the position of the shadows of the edges relative to the isocenter; and
adjusting the position of the source and/or the collimator along an axis substantially transverse to the collimator edges so as to position the shadows of the edges centrally about the isocenter.

6. The method according to claim 5, further comprising:
analyzing the image of the beam obtained from the first imaging device to determine the magnitude of asymmetry of beam intensity.

7. The method according to claim 6, further comprising:
rotating the source about the axis so as to reduce the magnitude of asymmetry of the beam intensity.

8. The method according to claim 7, wherein the rotating is about an axis substantially parallel to the collimator edges.

9. The method according to claim 7, further comprising:
rotating the source about an axis substantially perpendicular to the collimator edges.

10. The method according to claim 9, wherein at least one object is located between the source and the first imaging device, the object comprising at least one marker adapted to be visible in an image of the object produced by the beam in the first imaging device, the method further comprising:
obtaining the image of the object; and
determining the position of the object from a position of the at least one marker.

11. The method according to claim 10, wherein a third imaging device is positioned between the source and the first imaging device, the method further comprising:
irradiating an object with the beam and obtaining pairs of simultaneous images, wherein each pair includes a first image of the object obtained using the first imaging device and a second image obtained simultaneously using the third imaging device; and
comparing the position of at least one feature of the object in at least one pair of simultaneous images to determine the position of the third imaging device relative to the isocenter.

12. A method performed in a radiotherapy system, the radiotherapy system comprising a source for producing a beam of radiation, a first imaging device for imaging from the beam, the source and the first imaging device mounted so as to be rotatable about an axis perpendicular to the direction of the beam, and a collimator having collimating edges to collimate the beam, the method aligning the beam using a fiducial phantom including a plurality of markers and at least one non-symmetric feature when viewed from the first imaging device, the fiducial phantom being located between the source and the imaging device, the method comprising:
positioning the collimator edges so that when the collimator edges are illuminated by the beam, the collimator edges cast shadows detected by the imaging device;
determining, from an image of the fiducial phantom, the position of the source and the position of the shadows of the collimator edges relative to the isocenter;
adjusting the position of at least one of the source and the collimator along an axis substantially transverse to the collimator edges so as to position the shadows of the collimator edges centrally about the isocenter;
rotating the source and imaging device in a trajectory about the axis while obtaining a plurality of images of the fiducial phantom from a plurality of different angles;
determining from the locations of the markers in each image of the plurality of images of the fiducial phantom, a position of the source at the rotational position the image was obtained; and calculating the center of rotation of the positions of the source to define the isocenter of the radiotherapy system.

13. The method according to claim 12, further comprising:
calibrating the trajectory in relation to a gantry angle through analysis of at least one non-symmetric feature of the fiducial phantom included in each image.

14. The method according to claim 13, wherein the fiducial phantom comprises markers visible to MRI, the method further comprising:
scanning the fiducial phantom with an MR scanner which has an imaging field so as to align the source with the imaging field.

15. The method according to claim 14, further comprising:
analyzing the image of the beam obtained from the imaging device to determine the magnitude of asymmetry of beam intensity.

16. The method according to claim 15, further comprising:
rotating the source about the axis so as to reduce the magnitude of asymmetry of the beam intensity.

17. The method according to claim 16, wherein the rotating is about an axis substantially parallel to the collimator edges.

18. The method according to claim 16, further comprising:
rotating the source about an axis substantially perpendicular to the collimator edges.

19. The method according to claim 18, wherein at least one object is located between the source and the imaging device, the object comprising at least one marker adapted to be visible in an image of the object produced by the beam in the imaging device, the method further comprising:
obtaining the image of the object; and
determining at least one of the position and orientation of the object from at least one of the position and orientation of the marker, respectively.

20. The method according to claim 19, wherein the imaging device is a first imaging device and wherein a second imaging device is positioned between the source and the first imaging device, the method further comprising:
irradiating an object with the beam and obtaining pairs of simultaneous images, wherein each pair includes a first image of the object obtained using the first imaging device and a second image obtained simultaneously using the second imaging device; and
comparing the position of at least one feature of the object in at least one pair of simultaneous images to determine the position of the second imaging device relative to the isocenter.

* * * * *